(12) United States Patent
Bresee et al.

(10) Patent No.: US 6,344,872 B1
(45) Date of Patent: Feb. 5, 2002

(54) SYSTEM FOR TRANSPORTING AND IMAGING A TEXTILE MATERIAL

(75) Inventors: Randall R. Bresee, Knoxville, TN (US); Chang H. Hsi, Gaithersburg, MD (US)

(73) Assignee: The University of Tennessee Research Corporation

( * ) Notice: Subject to any disclaimer, the term of this patent is extended or adjusted under 35 U.S.C. 154(b) by 0 days.

(21) Appl. No.: 09/362,536

(22) Filed: Jul. 28, 1999

(51) Int. Cl.[7] .............................................. H04N 07/18
(52) U.S. Cl. ........................................... 348/88; 348/89
(58) Field of Search ............................ 348/88, 89, 90, 348/91, 92, 128, 129; 382/111

(56) References Cited

U.S. PATENT DOCUMENTS 5,774,177 A * 6/1998 Lane ............................. 348/88
5,936,665 A * 8/1999 Vachtsevanos et al. ....... 348/91
6,236,429 B1 * 5/2001 Ho ............................... 348/99

* cited by examiner

Primary Examiner—Andy Rao
(74) Attorney, Agent, or Firm—Duane, Morris & Heckscher LLP

(57) ABSTRACT

The present invention relates to a system for transporting and imaging a textile material. In particular, the present invention is directed toward a system comprising a motorized conveyor capable of moving a sheet of textile material around the far outer surface of an upper rod such that the portion of the textile material extending around the far outer surface of the upper rod can be imaged by a camera.

20 Claims, 4 Drawing Sheets

SYSTEM FOR TRANSPORTING AND IMAGING A TEXTILE MATERIAL

BACKGROUND OF THE INVENTION

1. Field of the Invention

The present invention relates to a system for transporting and imaging a textile material. In particular, the present invention is directed toward a system comprising a motorized conveyor capable of moving a sheet of textile material around the far outer surface of an upper rod such that the portion of the textile material extending around the far outer surface of the upper rod can be imaged by a camera.

2. Description of the Prior Art

Cameras have been used in conjunction with conveyor systems for moving sheets of textile material in order to capture images of the material. In such systems, the portion of the textile material that is imaged is typically a flat portion lying in a horizontal plane on the conveyor system. Such a fabric imaging system is disclosed in U.S. Pat. Nos. 5,774,177 to Lane and 5,095,835 to Jernigan, et al. Such systems are typically limited to providing a top view of the textile material being imaged.

Images produced by top view imaging systems are normally composed of structural features of interest such as fuzz and pills against a complicated background of varying brightness and/or darkness. This complicated background often comprises fibers, yarns, bonded points, and other fabric structural features. Top view images provide limited contrast which limits the amount of information which can be ascertained from analyzing the image at a given magnification level.

For certain fabrics, it is often useful and/or desirable to obtain a side view of the fabric. Such views are particularly useful in analyzing fuzz and/or pills in the fabric. The term fuzz as used herein, refers to fibers that are partially or completely teased out of a fabric. Fibers typically have diameters in the range of 5–25 micrometers. Due to their small size, they are difficult to detect in top view images.

The term pill, as used herein, refers to a small accumulation of entangled fibers on the surface of a fabric. Pills, which can develop during wear, are held to the fabric by an entanglement with the surface fibers of the material and are usually composed of the same fibers from which the fabric is made.

The present invention provides a means of rotating a textile fabric around the far side of an upper rod such that fabric structural features such as fuzz and pills extend horizontally outward into an illumination and imaging field where a side view of the fabric can be obtained. The present invention provides a system capable of capturing high quality images of a textile material, suitable for analyzing pills as well as the density, height, and separability of fuzz of the textile material.

Side view images, such as those obtainable from using the present invention, are less complex than top view images. Side view images typically comprise images of dark fuzz and pills against a uniformly bright background. Accordingly, such images provide greater information during analysis at a given magnification level than are provided by top view images. Side view images are particularly advantageous when one desires to perform image analysis of fibers, because of the greater ease in detecting fibers in side view images.

SUMMARY OF THE INVENTION

The present invention is directed toward a system for transporting and imaging a textile material comprising a support structure comprising a support area defining a plane, and a motorized conveyor mounted on the support structure. The conveyor comprises a movement axis and is capable of moving a textile material in either direction of the movement axis.

The invention further comprises an upper rod having a far outer surface which faces away from the support structure. The upper rod is positioned substantially perpendicular to the conveyor movement axis. An upper rod mounting arm has a first end connected to the upper rod and a second end connected to the support structure.

The invention further comprises a lower rod having a near outer surface which faces toward the support structure. The lower rod is positioned substantially parallel to and below the upper rod and is positioned closer to the support structure than the upper rod. A lower rod mounting arm has a first end connected to the lower rod and a second end connected to the support structure.

The invention further comprises an illumination source mounted below the upper rod and positioned to illuminate a textile material extending around the far outer surface of the upper rod. A camera is positioned above the illumination source so as to acquire images of a textile material extending around the far outer surface of the upper rod. A camera mounting structure is attached to the camera so as to allow linear movement of the camera perpendicular and parallel to the support area, and to allow rotational movement of the camera in a plane parallel to the support area.

The invention may also comprise a motorized linear rail to move the support structure along a movement axis perpendicular to the conveyor movement axis.

The invention further comprises a computer electronically coupled to the conveyor to selectively control the operation of the conveyor, linear rail and/or camera.

DESCRIPTION OF THE PREFERRED EMBODIMENTS

Figure 1:
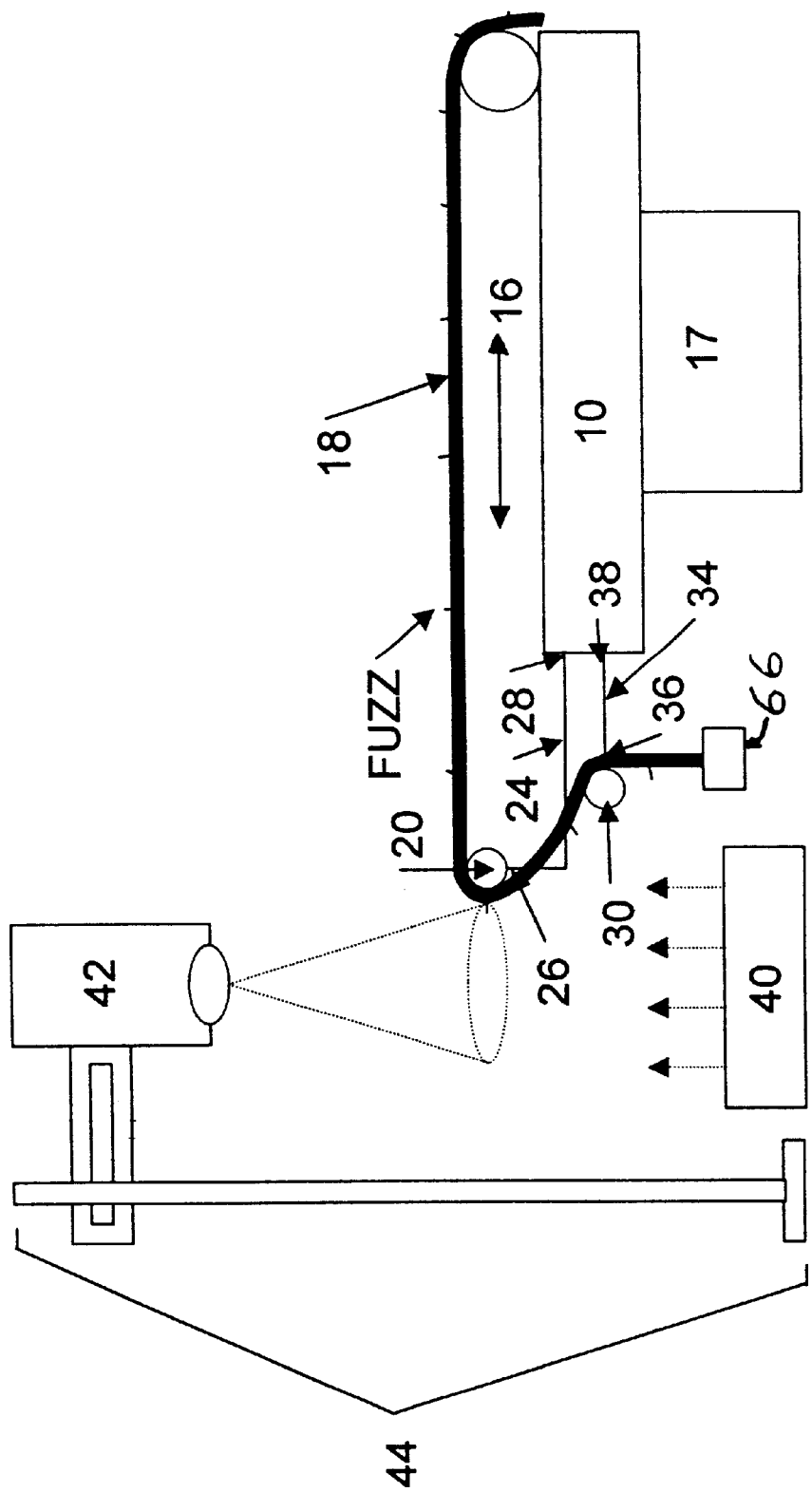
FIG. 1 is a side view of the present invention.
Figure 2:
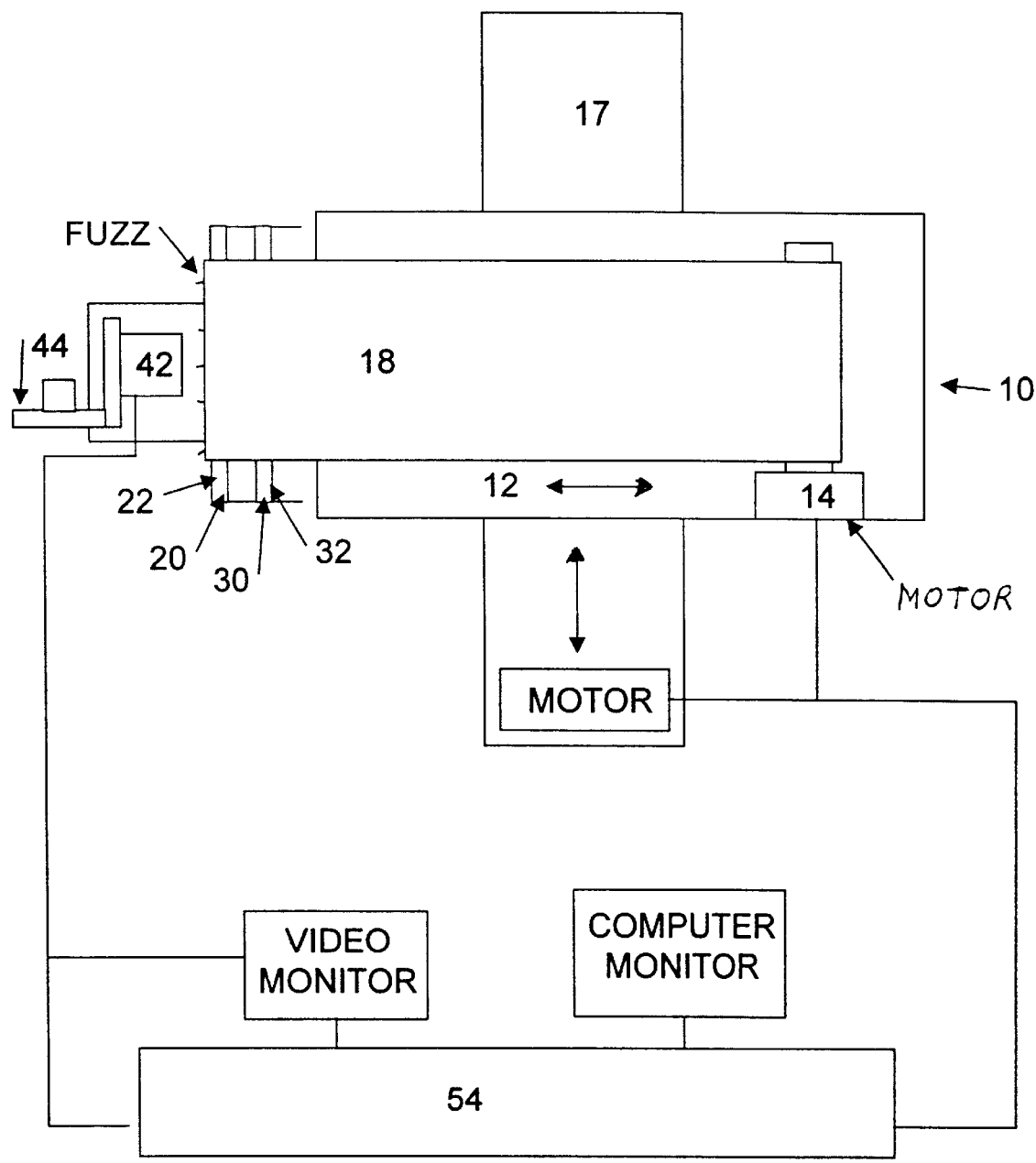
FIG. 2 is a top view of the present invention.

The present invention is directed toward a system for transporting and imaging a textile material comprising a support structure 10 comprising a support area 12 defining a support plane, as shown in FIGS. 1–2. In a preferred embodiment, the support area is a flat planar surface.

The invention further comprises a motorized conveyor 14 mounted on the support structure and comprising a movement axis 16 as shown in FIG. 1. In a preferred embodiment, the motion of the motorized conveyor is controller by a stepper motor. The conveyor is capable of moving a textile material 18 in either direction of the movement axis, as shown in FIGS. 1–2.

In a preferred embodiment, the motorized conveyor comprises a motorized roller capable of rotatably engaging a textile material. The diameter of the roller will be a function of the textile material being imaged. Roller diameters in the range of 1.0 to 150 millimeters should be appropriate for most textile materials.

The invention further comprises an upper rod 20 having a far outer surface 22 which faces away from the support structure, as shown in FIG. 2. The upper rod is positioned substantially perpendicular to the conveyor movement axis. In a preferred embodiment, the upper rod is rotatable. The diameter of the upper rod will be a function of the textile material being imaged. In a preferred embodiment, the diameter of the upper rod is in a range of 0.5 to 150 millimeters.

An upper rod mounting arm 24 has a first end 26 connected to the upper rod and a second end 28 connected to the support structure, as shown in FIG. 1.

The invention further comprises a lower rod 30 having a near outer surface 32 which faces toward the support structure, as shown in FIGS. 1–2. The lower rod is positioned substantially parallel to and below the upper rod and is positioned closer to the support structure than the upper rod, as shown in FIG. 1. In a preferred embodiment, the lower rod is rotatable.

A lower rod mounting arm 34 has a first end 36 connected to the lower rod and a second end 38 connected to the support structure, as shown in FIG. 1.

In a preferred embodiment, the textile material comprises fibers and has a first section attached to the conveyor, a second section extending between the conveyor and the upper rod, a third section wrapped around at least a portion of the far outer surface of the upper rod, a fourth section extending between the upper rod and lower rod, a fifth section wrapped around at least a portion of the near outer surface of the lower rod, and a sixth section extending below the lower rod. In a preferred embodiment, the textile material is attached to the conveyor by an attachment device, such as a mechanical clip or fastener, positioned to attach the material to the motorized roller.

In a preferred embodiment, weight 66 may be attached to the sixth section of the textile material so as to place a tension upon the textile material. The magnitude of the weight is a function of the fabric from which the textile material is made. In a preferred embodiment, the weight would be less than one kilogram per 1 cm width of the textile material.

The invention further comprises an illumination source 40 mounted below the upper rod and positioned to illuminate a textile material extending around the far outer surface of the upper rod, as shown in FIG. 1. In a preferred embodiment, the illumination source will produce an intensity variation over the illumination surface area of less than ±15% of the mean light intensity. An illumination source suitable for use in practicing the present invention is an Intralux dc-2100, with Backlight FiberOptic Attachment, made by Volpi Manufacturing USA of Auburn, N.Y.

A camera 42 is positioned above the illumination source so as to acquire images of a textile material extending around the far outer surface of the upper rod, as shown in FIG. 1. In a preferred embodiment, the camera is a digital camera electrically coupled to the computer. In another preferred embodiment, the camera is an analog camera electrically coupled to the computer which is capable of digitizing analog signals from the camera. Cameras suitable for use in practicing the present invention model include a TM 9700 by Pulnix of Sunnyvale, Calif., or a Model 68 by Dage MTI of Michigan City, Ind.

In a preferred embodiment, the invention may also include a video monitor 41 for displaying images from a camera or computer. The video monitor is electrically coupled to receive and display images from either the camera or the computer.

Figure 3:
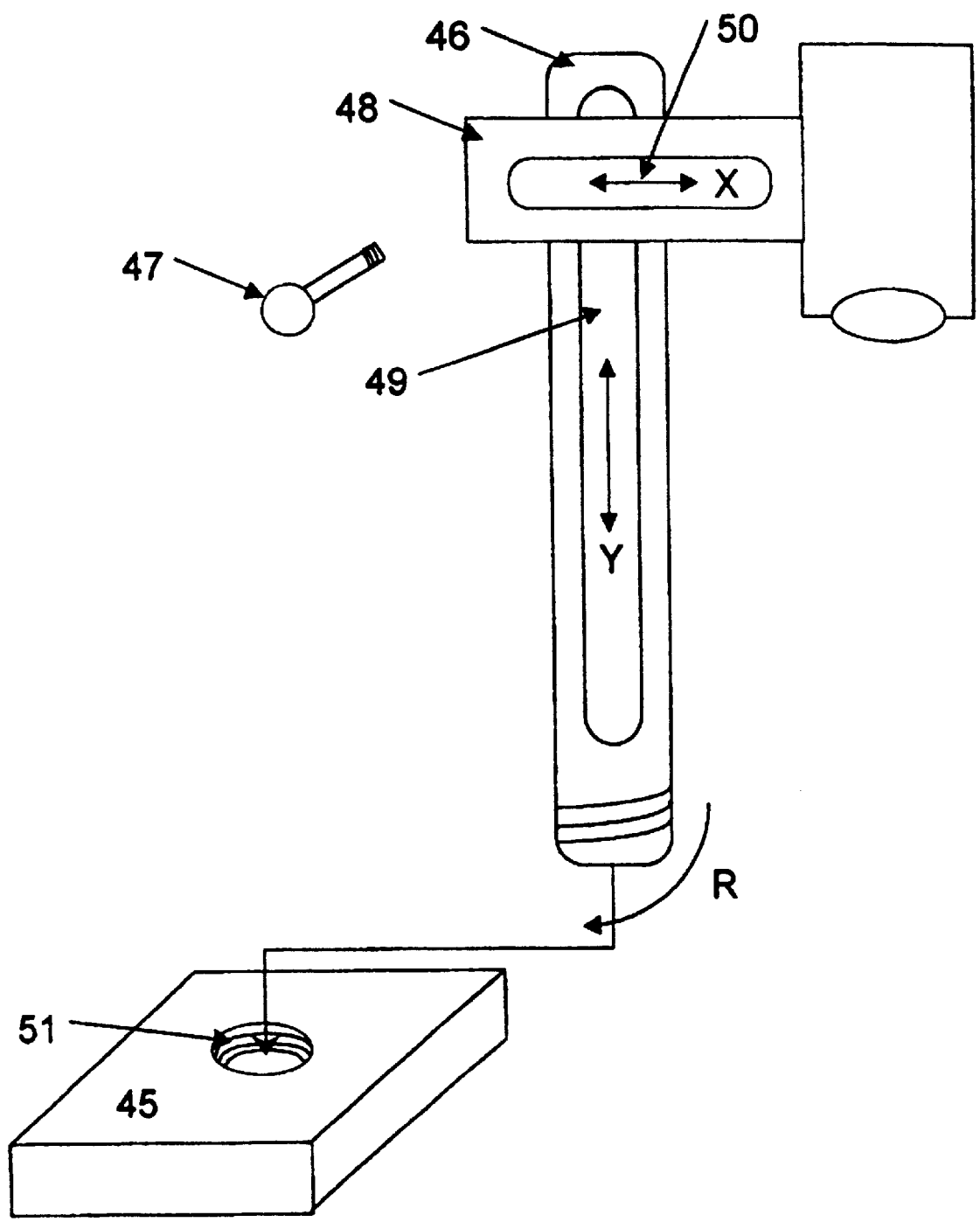
FIG. 3 is an exploded isometric view of the camera and mounting arm of the present invention.

A camera mounting structure 44 is attached to the camera so as to allow linear movement of the camera perpendicular and parallel to the support area, as shown in FIGS. 1 and 3. The linear movement of the camera perpendicular to the support area permits the camera lens to be focused in the focal plane positioned at the edge of a textile material extending around the far outer surface of the upper rod. The linear movement of the camera parallel to the support area permits the camera image field to be positioned at the edge of the textile material. The mounting structure is capable of allowing rotational movement of the camera in a plane parallel to the support area. The rotational movement of the mounting structure allows the camera image field to be aligned parallel to the upper rod.

The mounting structure comprises a base 45 comprising a base receptacle 51, as shown in FIG. 3. The mounting structure further comprises a rotatable pole 46, having a lower end received within the base receptacle 51. The rotatable pole 46 may be rotated in base receptacle 51, about rotational axis R in FIG. 3. Rotatable pole 46 further comprises a vertical pole channel 49, as shown in FIG. 3.

The mounting structure further comprises sliding bracket 48, comprising a horizontal bracket channel 50, as shown in FIG. 3. The sliding bracket is attached to the camera, as shown in FIG. 3. Locking device 47 extends through horizontal bracket channel 50, through vertical pole channel 49. A locking nut may be used to receive the portion of locking device 47 which extends through vertical pole channel 49. Locking device 47 can be loosened, thereby permitting the camera 44 to move up and down along axis Y in vertical pole channel 49, as shown in FIG. 3. Additionally, when locking device 47 is loosened, the sliding bracket 48 may be moved back and forth along axis X in horizontal bracket channel 50, as shown in FIG. 3.

Figure 4:
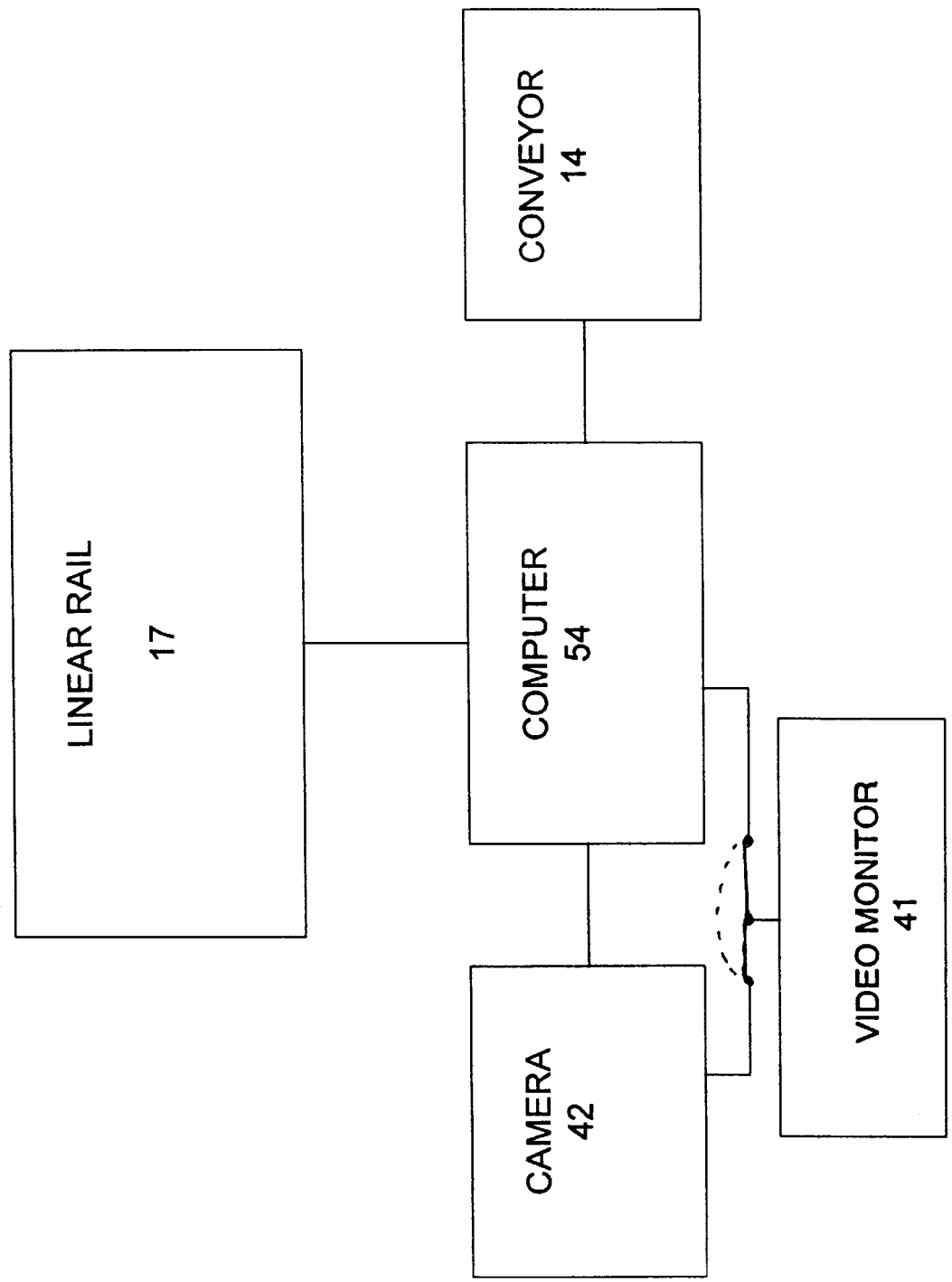
FIG. 4 is a block diagram of the computer, conveyor, camera, and motorized linear rail of the present invention.

The invention further comprises a computer 54 electrically coupled to the conveyor to selectively control the operation of the conveyor as shown in FIGS. 2 and 4. In a preferred embodiment the computer is also electrically coupled to the camera to control its operation. In this manner, the computer can be preprogramed to position a desired portion of textile material at a desired location before actuating the camera to capture an image of the textile material. Computers suitable for use in practicing the present invention include desktop personal computers comprising Pentium® III microprocessors, such as those available from Gateway Computers of North Sioux City, S.D., Dell Computer Corporation of Round Rock, Tex. and IBM Corporation of Armonk, N.Y. In a preferred embodiment, the computer may be an IBM PC300 or a Dell Optiflex or Dimension class PC.

In a preferred embodiment, the invention comprises a motorized linear rail 17 which is electrically coupled to the computer and upon which the support structure is movably mounted such that it may be selectively moved in either direction perpendicular to the conveyor movement axis, as shown in FIGS. 1, 2 and 4. In this embodiment, the textile material mounted on the invention can be selectively moved in two dimensions in a plane parallel to the support plane. In another preferred embodiment, the motion of the linear rail is controlled by a stepper motor which is coupled to the computer.

The foregoing disclosure and description of the invention are illustrative and explanatory. Various changes in the size, shape, and materials, as well as in the details of the illustrative embodiments may be made without departing from the spirit of the invention.

What is claimed is:

1. A system for transporting and imaging a textile material comprising:

a. a support structure comprising a support area defining a support plane;
b. a motorized conveyor mounted on said support structure and comprising a movement axis, said conveyor capable of moving a textile material in either direction of said movement axis;
c. an upper rod having a far outer surface which faces away from said support structure, said upper rod being positioned substantially perpendicular to said movement axis;
d. an upper rod mounting arm having a first end connected to said upper rod and a second end connected to said support structure;
e. a lower rod having a near outer surface which faces toward said support structure, said lower rod being positioned substantially parallel to and below said upper rod and being positioned closer to said support structure than said upper rod;
f. a lower rod mounting arm having a first end connected to said lower rod and a second end connected to said support structure;
g. an illumination source mounted below said upper rod and positioned to illuminate a textile material extending around the far outer surface of said upper rod;
h. a camera positioned above said illumination source so as to acquire images of a textile material extending around the far outer surface of said upper rod; and
i. a computer electrically coupled to said conveyor to selectively control the operation of said conveyor.

2. The system of claim 1 further comprising a camera mounting structure attached to said camera so as to allow linear movement of the camera perpendicular and parallel to said support area, and to allow rotational movement in a plane parallel to said support area.

3. The system of claim 1 wherein said upper rod and said lower rod are rotatable.

4. The system of claim 1 wherein said motorized conveyor comprises a motorized roller capable of rotatably engaging a textile material.

5. The system of claim 1 wherein said camera is a digital camera.

6. The system of claim 5 further comprising a video monitor electrically coupled to said digital camera directly or through said computer, said monitor being capable of receiving and displaying images from said camera.

7. The system of claim 1 wherein said computer is capable of digitizing analog signals from said camera, and said camera is an analog camera electrically coupled to said computer.

8. The system of claim 7 wherein said computer is capable of receiving and displaying images from said camera and further comprising a video monitor electrically coupled to said camera, said coupling being direct or through said computer.

9. The system of claim 1 wherein said computer is electrically coupled to said camera to selectively control its operation.

10. The system of claim 1 further comprising a motorized linear rail which is electrically coupled to said computer and upon which said support structure is movably mounted such that it may be selectively moved in either direction perpendicular to said movement axis.

11. The system of claim 1, further comprising a textile material comprising fibers and having a first section attached to said conveyor, a second section extending between said conveyor and said upper rod, a third section wrapped around at least a portion of the far outer surface of said upper rod, a fourth section extending between the upper rod and lower rod, a fifth section wrapped around at least a portion of the near outer surface of said lower rod, and a sixth section extending below said lower rod.

12. The system of claim 11 further comprising a weight less than 1.0 kg per 1 cm width of the textile material attached to said sixth section of textile material.

13. The system of claim 1, wherein the illumination source has an intensity variance over the illumination area less than ±15% of the mean light intensity.

14. The system of claim 2 wherein said camera mounting structure comprises:
a. a sliding bracket attached to said camera, said bracket comprising a horizontal bracket channel;
b. a rotatable pole comprising a vertical pole channel;
c. a locking device extending through the horizontal bracket channel and releasably secured within the vertical pole channel; and
d. a base comprising a base receptacle, said base receptacle being rotatably connected to said rotatable pole.

15. A system for transporting and imaging a textile material comprising:
a. a support structure comprising a support area defining a support plane;
b. a motorized conveyor mounted on said support structure and comprising a movement axis, said conveyor capable of moving a textile material in either direction of said movement axis;
c. an upper rod having a far outer surface which faces away from said support structure, said upper rod being positioned substantially perpendicular to said movement axis;
d. an upper rod mounting arm having a first end connected to said upper rod and a second end connected to said support structure;
e. a lower rod having a near outer surface which faces toward said support structure, said lower rod being positioned substantially parallel to and below said upper rod and being positioned closer to said support structure than said upper rod;
f. a lower rod mounting arm having a first end connected to said lower rod and a second end connected to said support structure;
g. an illumination source mounted below said upper rod and positioned to illuminate a textile material extending around the far outer surface of said upper rod;
h. a camera positioned above said illumination source so as to acquire images of a textile material extending around the far outer surface of said upper rod;
i. a sliding bracket attached to said camera, said bracket comprising a horizontal bracket channel;
j. a base comprising a base receptacle;
k. a rotatable pole comprising a vertical pole channel, said rotatable pole being rotatably inserted into said base receptacle;
l. a locking device extending through the horizontal bracket channel and releasably secured within said vertical pole channel; and
m. a computer electrically coupled to said conveyor and to said camera, to selectively control the operation of said conveyor and said camera.

16. The system of claim 15 further comprising a motorized linear rail which is electrically coupled to said computer and upon which said support structure is movably mounted such that it may be selectively moved in either direction perpendicular to said movement axis.

17. The system of claim 15, further comprising a textile material comprising fibers and having a first section attached to said conveyor, a second section extending between said conveyor and said upper rod, a third section wrapped around at least a portion of the far outer surface of said upper rod, a fourth section extending between the upper rod and lower rod, a fifth section wrapped around at least a portion of the near outer surface of said lower rod, and a sixth section extending below said lower rod.

18. The system of claim 15 wherein said camera is a digital camera and further comprising a video monitor electrically coupled to said digital camera, said coupling being direct or through a computer, and said monitor being capable of receiving and displaying images from said digital camera.

19. The system of claim 15 wherein said camera is an analog camera and further comprising:
   a. a computer coupled to said camera to digitize analog signals from said camera; and
   b. a video monitor electrically coupled to said analog camera directly or through said computer which is capable of receiving and displaying images from said camera.

20. A system for transporting and imaging a textile material comprising:
   a. a support structure comprising a support area defining a support plane;
   b. a motorized conveyor mounted on said support structure and comprising a movement axis, said conveyor capable of moving a textile material in either direction of said movement axis;
   c. a rotatable upper rod having a far outer surface which faces away from said support structure, said upper rod being positioned substantially perpendicular to said movement axis;
   d. an upper rod mounting arm having a first end connected to said upper rod and a second end connected to said support structure;
   e. a rotatable lower rod having a near outer surface which faces toward said support structure, said lower rod being positioned substantially parallel to and below said upper rod and being positioned closer to said support structure than said upper rod;
   f. a lower rod mounting arm having a first end connected to said lower rod and a second end connected to said support structure;
   g. an illumination source mounted below said upper rod and positioned to illuminate a textile material extending around the far outer surface of said upper rod;
   h. an analog camera positioned above said illumination source so as to acquire images of a textile material extending around the far outer surface of said upper rod; and
   i. a computer electrically coupled to said conveyor and to said camera to selectively control the operation of said conveyor and to receive analog signals from said camera, said computer being capable of digitizing analog signals from said camera.

* * * * *